(12) United States Patent
Shelton, IV et al.

(10) Patent No.: US 10,881,402 B2
(45) Date of Patent: Jan. 5, 2021

(54) SURGICAL END EFFECTOR ADJUNCT ATTACHMENT

(71) Applicant: Ethicon LLC, Guaynabo, PR (US)

(72) Inventors: Frederick E. Shelton, IV, Hillsboro, OH (US); Prudence Vulhop, Cincinnati, OH (US); Jason L. Harris, Lebanon, OH (US); Michael J. Vendely, Lebanon, OH (US); Greg Scott, Cincinnati, OH (US)

(73) Assignee: Ethicon LLC, Guaynabo, PR (US)

( * ) Notice: Subject to any disclaimer, the term of this patent is extended or adjusted under 35 U.S.C. 154(b) by 677 days.

(21) Appl. No.: 15/436,019

(22) Filed: Feb. 17, 2017

(65) Prior Publication Data

US 2018/0235622 A1 Aug. 23, 2018

(51) Int. Cl.
*A61B 17/072* (2006.01)
*A61B 17/00* (2006.01)
*A61B 17/115* (2006.01)

(52) U.S. Cl.
CPC .. *A61B 17/07207* (2013.01); *A61B 17/07292* (2013.01); *A61B 17/1155* (2013.01);
(Continued)

(58) Field of Classification Search
CPC ....... A61B 17/068–07292; A61B 2017/07214; A61B 2017/07278; A61B 17/07292; A61B 17/072
See application file for complete search history.

(56) References Cited

U.S. PATENT DOCUMENTS 5,632,432 A * 5/1997 Schulze ........... A61B 17/07207
227/176.1
5,702,409 A * 12/1997 Rayburn .......... A61B 17/07207
227/176.1
(Continued)

FOREIGN PATENT DOCUMENTS

EP 1994890 A1 11/2008
EP 2497431 A1 9/2012
(Continued)

OTHER PUBLICATIONS

Extended European Search Report for EP App. No. 18157212.4 dated May 2, 2018 (13 pages).

*Primary Examiner* — Katrina M Stransky
*Assistant Examiner* — Brigid K Byrd
(74) *Attorney, Agent, or Firm* — Mintz Levin Cohn Ferris Glovsky and Popeo, P.C.

(57) ABSTRACT

Various embodiments of a frame for attaching an adjunct to an end effector of a surgical device are provided. In one embodiment, the end effector can include upper and lower jaws, and the frame can include features for releasably engaging one or the jaws. The frame can also include retaining features for coupling an adjunct to a tissue-facing surface of the frame, thereby releasably coupling the adjunct material to the jaw of the end effector. In some implementations, the frame can include a plurality of retaining features that are configured to engage the adjunct material to create a tension in the adjunct material, which can further assist with securing the frame to the jaw. In other embodiments, a removable applicator member is provided for retaining at least one adjunct material and for aligning and coupling the adjunct material to a frame.

10 Claims, 10 Drawing Sheets

(52) U.S. Cl.
CPC ............. *A61B 2017/0046* (2013.01); *A61B 2017/00884* (2013.01); *A61B 2017/00893* (2013.01); *A61B 2017/07257* (2013.01)

(56) References Cited

U.S. PATENT DOCUMENTS

| | | | |
|---|---|---|---|
| 6,592,597 B2 * | 7/2003 | Grant ................... | A61B 17/072 |
| | | | 606/151 |
| 6,656,193 B2 * | 12/2003 | Grant ............... | A61B 17/07207 |
| | | | 606/151 |
| 7,143,925 B2 | 12/2006 | Shelton, IV et al. | |
| 7,601,118 B2 | 10/2009 | Smith et al. | |
| 8,317,070 B2 | 11/2012 | Hueil et al. | |
| 8,393,514 B2 | 3/2013 | Shelton, IV et al. | |
| 9,282,962 B2 | 3/2016 | Schmid et al. | |
| 2002/0165562 A1 * | 11/2002 | Grant ................... | A61B 17/072 |
| | | | 606/151 |
| 2007/0246505 A1 * | 10/2007 | Pace-Floridia .......................... | |
| | | | A61B 17/07207 |
| | | | 227/175.1 |
| 2008/0290134 A1 * | 11/2008 | Bettuchi ............. | A61B 17/068 |
| | | | 227/176.1 |
| 2009/0120994 A1 * | 5/2009 | Murray ........... | A61B 17/00491 |
| | | | 227/180.1 |
| 2012/0080498 A1 * | 4/2012 | Shelton, IV ....... | A61B 17/0643 |
| | | | 227/178.1 |
| 2012/0318844 A1 | 12/2012 | Shelton, IV et al. | |
| 2013/0068816 A1 * | 3/2013 | Mandakolathur Vasudevan ........ | |
| | | | A61B 17/07292 |
| | | | 227/175.1 |
| 2013/0105548 A1 * | 5/2013 | Hodgkinson ........ | A61B 17/072 |
| | | | 227/176.1 |
| 2013/0146642 A1 | 6/2013 | Shelton, IV et al. | |
| 2013/0214030 A1 | 8/2013 | Aronhalt et al. | |
| 2013/0221065 A1 | 8/2013 | Aronhalt et al. | |
| 2013/0256377 A1 | 10/2013 | Schmid et al. | |
| 2014/0158741 A1 * | 6/2014 | Woodard, Jr. ..... | A61B 17/0401 |
| | | | 227/175.1 |
| 2015/0129634 A1 | 5/2015 | Shelton, IV et al. | |
| 2015/0133995 A1 | 5/2015 | Shelton, IV et al. | |
| 2015/0133996 A1 | 5/2015 | Shelton, IV et al. | |
| 2015/0134076 A1 | 5/2015 | Shelton, IV et al. | |
| 2015/0134077 A1 | 5/2015 | Shelton, IV et al. | |
| 2015/0272575 A1 | 10/2015 | Leimbach et al. | |
| 2015/0277471 A1 | 10/2015 | Leimbach et al. | |
| 2015/0351758 A1 | 12/2015 | Shelton, IV et al. | |
| 2016/0089142 A1 | 3/2016 | Harris et al. | |
| 2017/0055986 A1 | 3/2017 | Harris et al. | |

FOREIGN PATENT DOCUMENTS

| | | |
|---|---|---|
| EP | 2517637 A1 | 10/2012 |
| EP | 2687165 A1 | 1/2014 |
| EP | 2865344 A1 | 4/2015 |

* cited by examiner

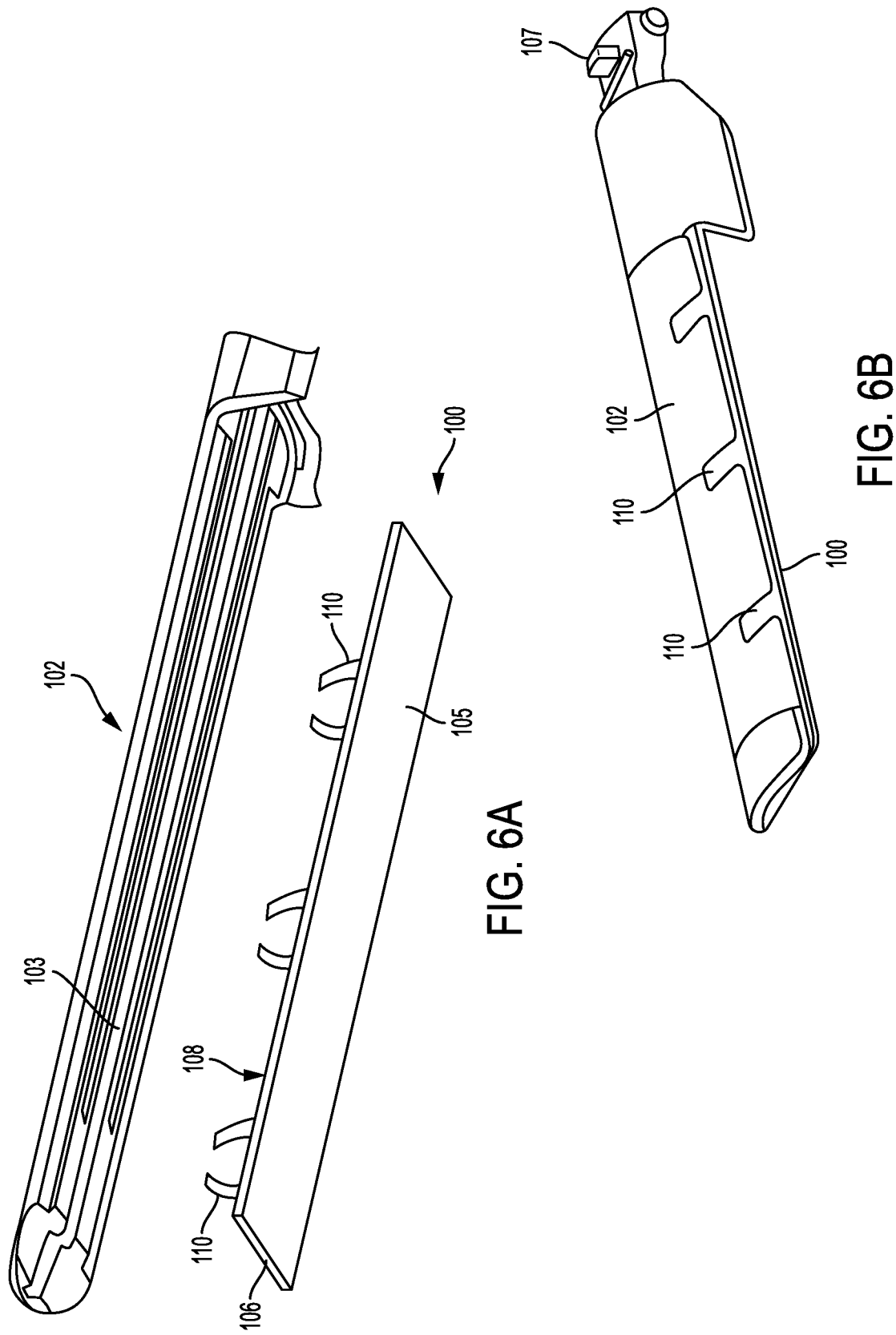

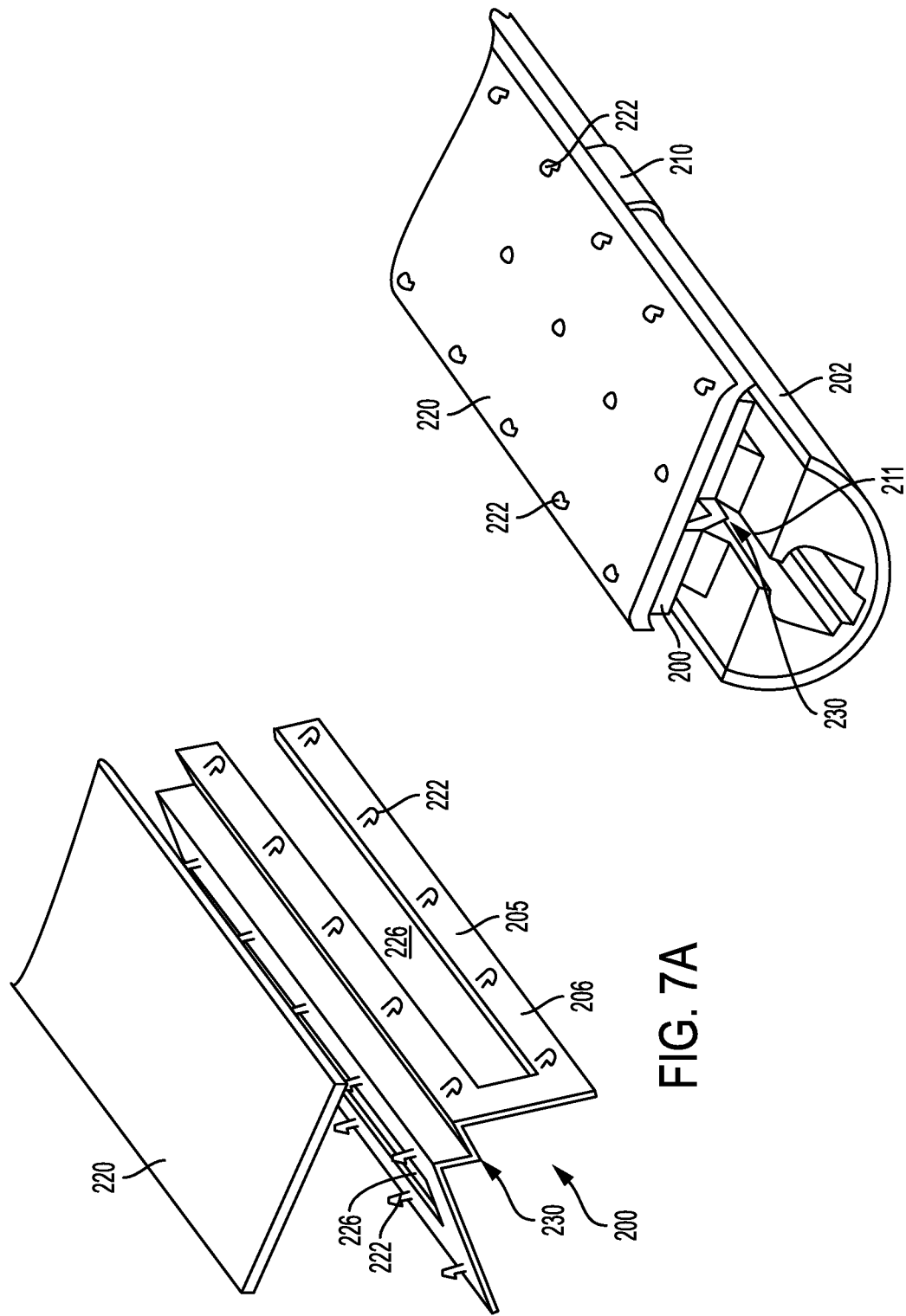

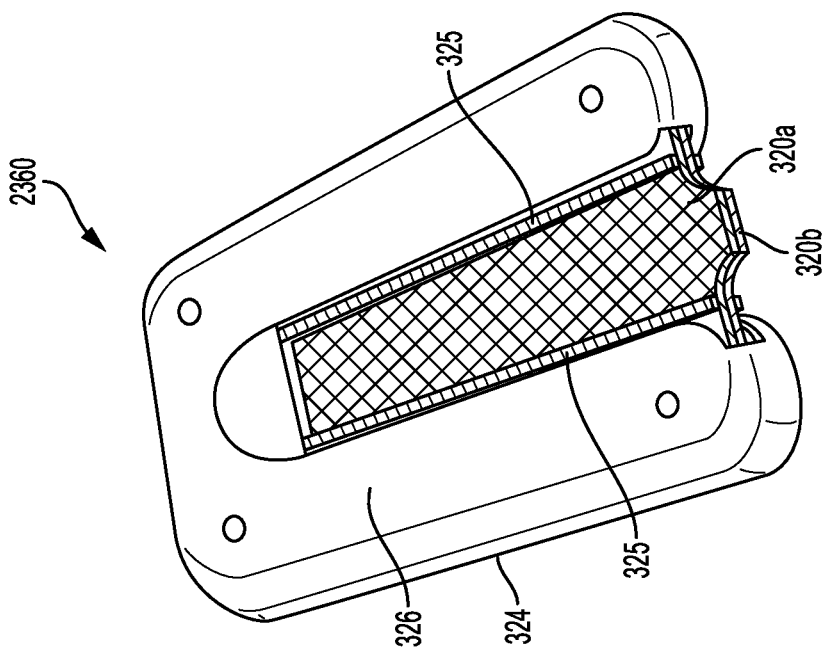
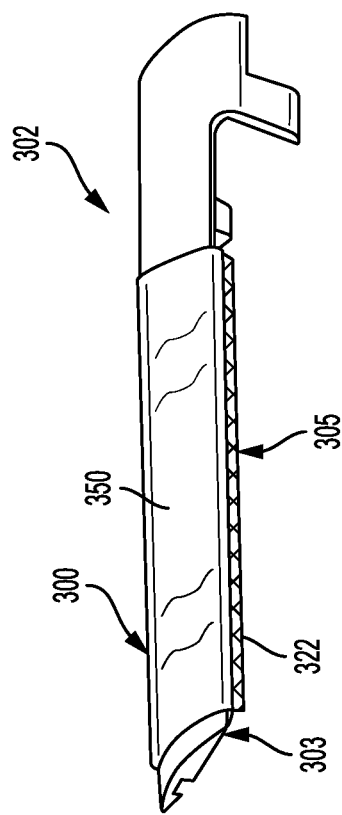
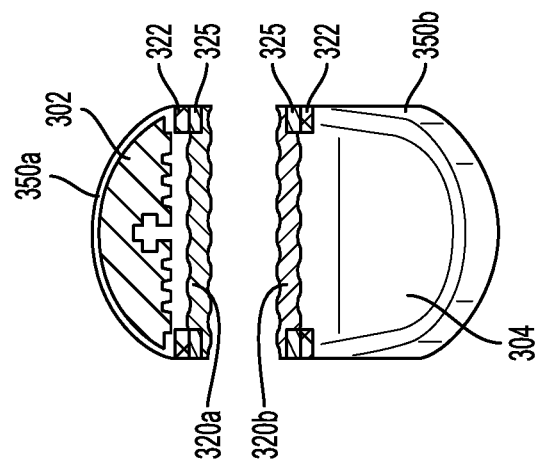
FIG. 8C
FIG. 8A
FIG. 8B

SURGICAL END EFFECTOR ADJUNCT ATTACHMENT

FIELD

Methods and devices are provided for securing one or more adjunct materials to an end effector of a surgical instrument.

BACKGROUND

Surgical staplers are used in surgical procedures to close openings in tissue, blood vessels, ducts, shunts, or other objects or body parts involved in the particular procedure. The openings can be naturally occurring, such as passageways in blood vessels or an internal organ like the stomach, or they can be formed by the surgeon during a surgical procedure, such as by puncturing tissue or blood vessels to form a bypass or an anastomosis, or by cutting tissue during a stapling procedure.

Most staplers have a handle with an elongate shaft having an end effector with a pair of movable opposed jaws for engaging and stapling tissue. The staples are typically contained in a staple cartridge, which can house multiple rows of staples and that is often disposed in one of the jaws for ejection of the staples to the surgical site. In use, the jaws are positioned to engage tissue, and the device is actuated to eject staples through the tissue. Some staplers include a knife configured to travel between rows of staples in the staple cartridge to longitudinally cut the stapled tissue between the stapled rows.

While surgical staplers have improved over the years, a number of problems still present themselves. One common problem is that leaks can occur due to the staple forming holes when penetrating the tissue or other object in which it is disposed. Blood, air, gastrointestinal fluids, and other fluids can seep through the openings formed by the staples, even after the staple is fully formed. The tissue being treated can also become inflamed due to the trauma that results from stapling. Still further, staples, as well as other objects and materials that can be implanted in conjunction with procedures like stapling, generally lack some characteristics of the tissue in which they are implanted. For example, staples and other objects and materials can lack the natural flexibility of the tissue in which they are implanted. A person skilled in the art will recognize that it is often desirable for tissue to maintain as much of its natural characteristics as possible after staples are disposed therein.

Accordingly, there remains a need for improved devices and methods for stapling tissue, blood vessels, ducts, shunts, or other objects or body parts such that leaking and inflammation is minimized while substantially maintaining the natural characteristics of the treatment region.

SUMMARY

Methods, systems, and devices are provided for releasably retaining a frame with an adjunct to a jaw of an end effector of a surgical instrument. In one embodiment, an end effector is provided and can include first and second jaws. The first and second jaws can be movably coupled to one another and can be configured to engage tissue therebetween, as well as fire a plurality of surgical staples into tissue. The end effector can further include a frame having at least one retaining feature configured to releasably engage the first jaw, and an adjunct material releasably secured to a tissue-facing surface of the frame.

In one embodiment, the frame can be in the form of an elongated planar body extending along a tissue-facing surface of the first jaw. The frame can include at least one pair of attachment arms that extend from opposed sides thereof and that are configured to grasp opposed sides of the first jaw. In certain aspects, the first jaw can include at least one pair of recesses formed in the opposed sides thereof that are configured to seat the at least one pair of attachment arms to prevent sliding of the frame relative to the first jaw. The frame can also include at least one opening that extends longitudinally along a length thereof and that is configured to allow one or more staples to be delivered therethrough for stapling the adjunct material to tissue engaged between the first and second jaws.

In one embodiment, the frame can include a hinge that is configured to extend into a knife slot formed in the first jaw. The hinge can extend along a longitudinal axis of the frame and can be configured to apply tension to the adjunct. The adjunct material and a part of the hinge can be configured to be cut by a knife translating along the knife slot. The frame can be configured to release the adjunct material when the hinge is cut by the knife. In certain aspects, the at least one retaining feature can include at least one hook configured to apply tension across the adjunct material when the adjunct is coupled to the frame.

In another embodiment, the frame can be in the form of an overlay configured to slide over and extend around the first jaw. The overlay can include an adhesive for securing a position of the overlay relative to the first jaw and/or the overlay can be flexible. The overlay can include at least one row of retaining features arranged to correspond with at least one row of complimentary retaining features positioned along the adjunct material for coupling the adjunct material to the overlay. The at least one row of complimentary retaining features can extend along opposing sides of the adjunct material between distal and proximal ends of the adjunct material.

Surgical methods are also provided, and in one embodiment the method includes releasably coupling a frame to a first jaw of an end effector with the frame having an adjunct material releasably secured thereto. Tissue can be engaged between the first jaw and a second jaw of the end effector, and the end effector can be activated to fire a plurality of staples through the adjunct and into the tissue. The frame can release the adjunct material such that the adjunct material remains stapled to the tissue.

In certain embodiments, the end effector can be activated to fire a plurality of staples and to cause a knife to cut the adjunct material such that the frame releases the adjunct material. The frame can be in the form of an overlay that is releasably coupled to the first jaw by adhering the overlay to the first jaw.

BRIEF DESCRIPTION OF DRAWINGS

This invention will be more fully understood from the following detailed description taken in conjunction with the accompanying drawings, in which:

FIG. 6A is an exploded view of one embodiment of a frame configured to couple to an adjunct material and a jaw;

FIG. 6B is a perspective top view of the frame coupled to the jaw of FIG. 6A;

FIG. 7A is an exploded view of another embodiment of a frame configured to couple to a jaw and an adjunct material;

FIG. 7B is a perspective top view of the frame coupled to the jaw of FIG. 7A, with the adjunct material coupled to a tissue-facing surface of the frame;

FIG. 8A is a perspective view of yet another embodiment of a frame configured as an overlay extending around a jaw with a tissue facing surface of the overlay having two rows of retaining features;

FIG. 8B is a cross-sectional view of a portion of an end effector of FIG. 8A showing a first overlay coupled to the jaw and a second overlay coupled to another jaw with a first and second adjunct material, respectively, releasably coupled thereon; and FIG. 8C is a perspective view of an applicator member configured to apply the first and second adjunct materials to the first and second overlays of FIG. 8B.

DETAILED DESCRIPTION

Figure 1:
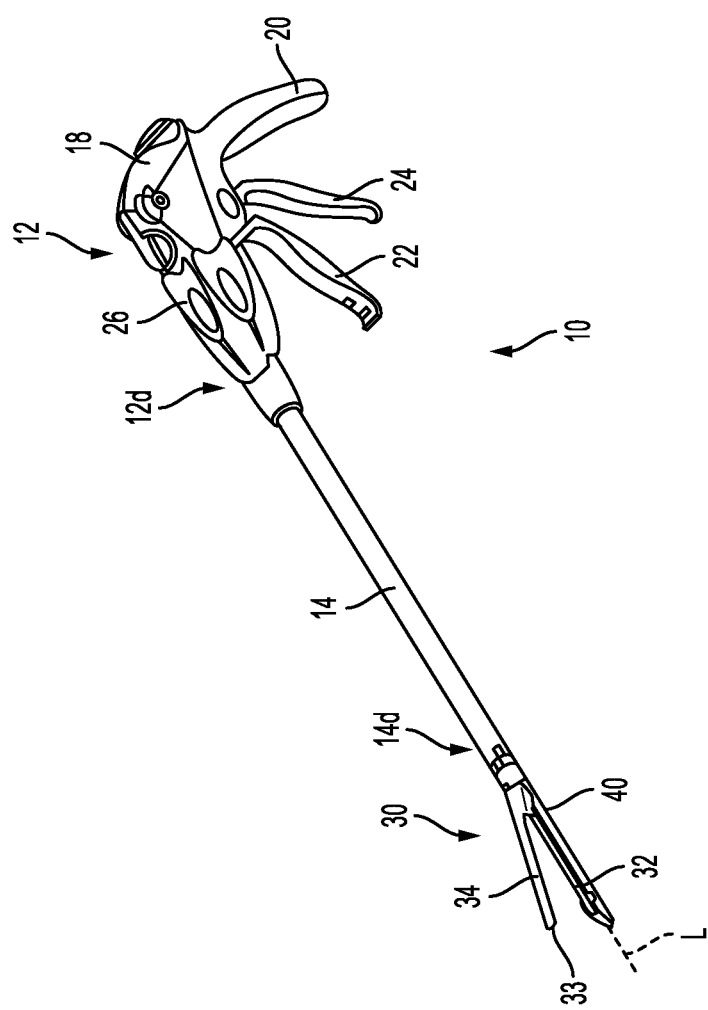
FIG. 1 is a perspective view of one embodiment of a surgical stapler.

Certain exemplary embodiments will now be described to provide an overall understanding of the principles of the structure, function, manufacture, and use of the devices and methods disclosed herein. One or more examples of these embodiments are illustrated in the accompanying drawings. Those skilled in the art will understand that the devices, systems, and methods specifically described herein and illustrated in the accompanying drawings are non-limiting exemplary embodiments and that the scope of the present invention is defined solely by the claims. The features illustrated or described in connection with one exemplary embodiment may be combined with the features of other embodiments. Such modifications and variations are intended to be included within the scope of the present invention.

Further, in the present disclosure, like-named components of the embodiments generally have similar features, and thus within a particular embodiment each feature of each like-named component is not necessarily fully elaborated upon. Additionally, to the extent that linear or circular dimensions are used in the description of the disclosed systems, devices, and methods, such dimensions are not intended to limit the types of shapes that can be used in conjunction with such systems, devices, and methods. A person skilled in the art will recognize that an equivalent to such linear and circular dimensions can easily be determined for any geometric shape. Sizes and shapes of the systems and devices, and the components thereof, can depend at least on the anatomy of the subject in which the systems and devices will be used, the size and shape of components with which the systems and devices will be used, and the methods and procedures in which the systems and devices will be used.

It will be appreciated that the terms "proximal" and "distal" are used herein with reference to a user, such as a clinician, gripping a handle of an instrument. Other spatial terms such as "front" and "back" similarly correspond respectively to distal and proximal. It will be further appreciated that for convenience and clarity, spatial terms such as "vertical" and "horizontal" are used herein with respect to the drawings. However, surgical instruments are used in many orientations and positions, and these spatial terms are not intended to be limiting and absolute.

In some embodiments, the devices and methods described herein are provided for open surgical procedures, and in other embodiments, the devices and methods are provided for laparoscopic, endoscopic, and other minimally invasive surgical procedures. The devices may be fired directly by a human user or remotely under the direct control of a robot or similar manipulation tool. However, a person skilled in the art will appreciate that the various methods and devices disclosed herein can be used in numerous surgical procedures and applications. Those skilled in the art will further appreciate that the various instruments disclosed herein can be inserted into a body in any way, such as through a natural orifice, through an incision or puncture hole formed in tissue, or through an access device, such as a trocar cannula. For example, the working portions or end effector portions of the instruments can be inserted directly into a patient's body or can be inserted through an access device that has a working channel through which the end effector and elongated shaft of a surgical instrument can be advanced.

It can be desirable to use one or more biologic materials and/or synthetic materials, collectively referred to herein as "adjuncts," in conjunction with surgical instruments to help improve surgical procedures. While a variety of different surgical end effectors can benefit from the use of adjuncts, in some exemplary embodiments the instrument can be a surgical stapler. When used in conjunction with a surgical stapler, the adjunct(s) can be disposed between and/or on jaws of the stapler, incorporated into a staple cartridge disposed in the jaws, or otherwise placed in proximity to the staples. When staples are deployed, the adjunct(s) can remain at the treatment site with the staples, in turn providing a number of benefits. For example, the adjunct(s) may reinforce tissue at the treatment site, preventing tearing or ripping by the staples at the treatment site. Tissue reinforcement may be needed to keep the staples from tearing through the tissue if the tissue is diseased, is healing from another treatment such as irradiation, medications such as chemotherapy, or other tissue property altering situation. In some instances, the adjunct(s) may minimize tissue movement in and around the staple puncture sites that can occur from tissue deformation that occurs after stapling (e.g., lung inflation, gastrointestinal tract distension, etc.). It will be recognized by one skilled in the art that a staple puncture site may serve as a stress concentration and that the size of the hole created by the staple will grow when the tissue around it is placed under tension. Restricting the tissues movement around these puncture sites can minimize the size the holes may grow to under tension. In some instances, the adjunct(s) can be configured to wick or absorb beneficial fluids, e.g., sealants, blood, glues, that further promote healing, and in some instances, the adjunct(s) can be configured to degrade to form a gel, e.g., a sealant, that further promotes healing. In some instances, the adjunct(s) can be used to help seal holes formed by staples as they are implanted into tissue, blood vessels, and various other objects or body parts. The adjunct(s) may also affect tissue growth through the spacing, positioning and/or orientation of any fibers or strands associated with the adjunct(s). Furthermore, in some circumstances, an adjunct can be useful in distributing pressure applied by the staple thereby reducing the possibility of a staple pulling through a tissue (which can be friable) and failing to fasten the tissue as intended (so-called "cheese wiring"). Additionally, the adjunct can be at least partially stretchable and can thus allow at least partial natural motion of the tissue (e.g., expansion and contraction of lung tissue during breathing). In some embodiments, a staple line can be flexible as described, for example, in U.S. Pat. Pub. No. 2016/0089142 entitled "Method for Creating a Flexible Staple Line," filed on Sep. 26, 2014, which is hereby incorporated by reference herein in its entirety.

Coupling an adjunct material to one or both jaws of an end effector can be tedious and time consuming for a user, which can undesirably prolong surgical procedures. Furthermore, surgical procedures can be prolonged when more than one adjunct material is applied to a jaw, such as for consecutive stapling with an adjunct material. As such, various adjunct frame embodiments are described herein that are configured to releasably attach an adjunct material thereto and to efficiently couple to a jaw of an end effector of a surgical instrument. The adjunct frames can thus provide an efficient way to couple an adjunct material to a jaw. The adjunct frames are also configured to release the adjunct material when desired, such as after the adjunct material has been cut by a knife of the end effector and/or after firing of staples by the end effector. The adjunct frames can release the adjunct material while maintaining coupling between the adjunct frame and the respective jaw. This can ensure that the frame is not left at the surgical site, which would require additional procedure time to retrieve the frame and could result in complications. Instead, the user can retract the end effector with the adjunct frame still attached, thereby allowing the user to reload the adjunct frame with another adjunct material or decouple the adjunct frame from the jaw.

Surgical Stapling Instruments

A variety of surgical instruments can be used in conjunction with the adjunct(s) and/or medicant(s) disclosed herein. "Adjuncts" are also referred to herein as "adjunct materials." The surgical instruments can include surgical staplers. A variety of surgical staplers can be used, for example linear surgical staplers and circular staplers. In general, a linear stapler can be configured to create longitudinal staple lines and can include elongate jaws with a cartridge coupled thereto containing longitudinal staple rows. The elongate jaws can include a knife or other cutting element capable of creating a cut between the staple rows along tissue held within the jaws. In general, a circular stapler can be configured to create annular staple lines and can include circular jaws with a cartridge containing annular staple rows. The circular jaws can include a knife or other cutting element capable of creating a cut inside of the rows of staples to define an opening through tissue held within the jaws. The staplers can be used on a variety of tissues in a variety of different surgical procedures, for example in thoracic surgery or in gastric surgery.

Figure 2:
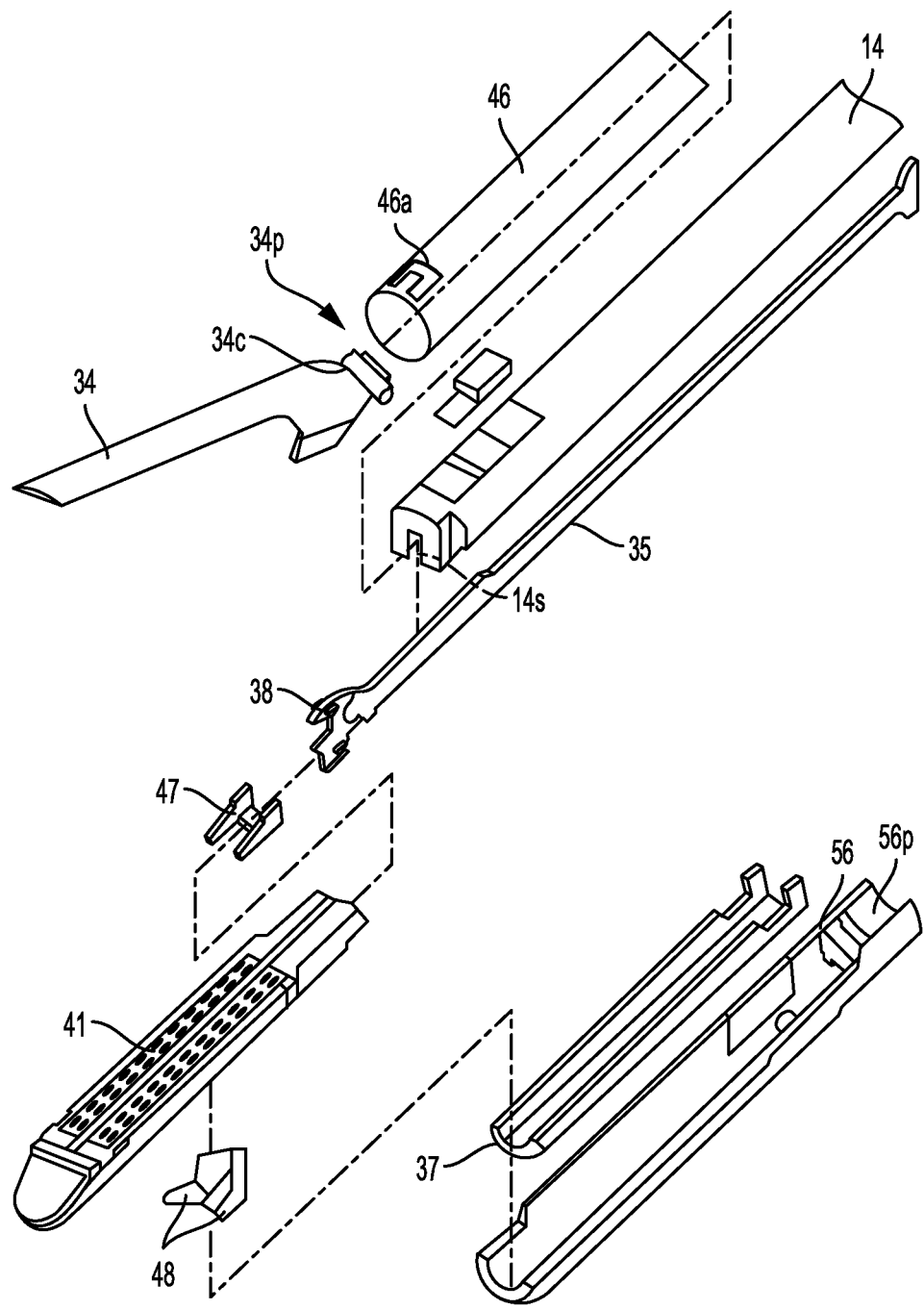
FIG. 2 is an exploded view of a distal portion of the surgical stapler of FIG. 1.

FIG. 1 illustrates one example of a linear surgical stapler 10 suitable for use with one or more adjunct(s) and/or medicant(s). The stapler 10 generally includes a handle assembly 12, a shaft 14 extending distally from a distal end 12d of the handle assembly 12, and an end effector 30 at a distal end 14d of the shaft 14. The end effector 30 has opposed lower and upper jaws 32, 34, although other types of end effectors can be used with the shaft 14, handle assembly 12, and components associated with the same. As shown in FIG. 2, the lower jaw 32 has a staple channel 56 (see FIG. 2) configured to support a staple cartridge 40, and the upper jaw 34 has an anvil surface 33 that faces the lower jaw 32 and that is configured to operate as an anvil to help deploy staples of the staple cartridge 40 (the staples are obscured in FIGS. 1 and 2). At least one of the opposed lower and upper jaws 32, 34 is moveable relative to the other lower and upper jaws 32, 34 to clamp tissue and/or other objects disposed therebetween. In some implementations, one of the opposed lower and upper jaws 32, 34 may be fixed or otherwise immovable. In some implementations, both of the opposed lower and upper jaws 32, 34 may be movable. Components of a firing system can be configured to pass through at least a portion of the end effector 30 to eject the staples into the clamped tissue. In various implementations a knife blade 36 (see FIG. 3) or other cutting element can be associated with the firing system to cut tissue during the stapling procedure. The cutting element can be configured to cut tissue at least partially simultaneously with the staples being ejected. In some circumstances, it may be advantageous if the tissue is cut after the staples have been ejected and the tissue is secured. Thus, if a surgical procedure requires that a tissue captured between the jaws be severed, the knife blade 36 is advanced to sever the tissue grasped between the jaws after the staples have been ejected from the staple cartridge 40.

Operation of the end effector 30 can begin with input from a user, e.g., a clinician, a surgeon, etc., at the handle assembly 12. The handle assembly 12 can have many different configurations designed to manipulate and operate the end effector 30 associated therewith. In the illustrated example, the handle assembly 12 has a pistol-grip type housing 18 with a variety of mechanical and/or electrical components disposed therein to operate various features of the instrument 10. For example, the handle assembly 12 can include a rotation knob 26 mounted adjacent the distal end 12d thereof which can facilitate rotation of the shaft 14 and/or the end effector 30 with respect to the handle assembly 12 about a longitudinal axis L of the shaft 14. The handle assembly 12 can further include clamping components as part of a clamping system actuated by a clamping trigger 22 and firing components as part of the firing system that are actuated by a firing trigger 24. The clamping and firing triggers 22, 24 can be biased to an open position with respect to a stationary handle 20, for instance by a torsion spring. Movement of the clamping trigger 22 toward the stationary handle 20 can actuate the clamping system, described below, which can cause the jaws 32, 34 to collapse towards each other and to thereby clamp tissue therebetween. Movement of the firing trigger 24 can actuate the firing system, described below, which can cause the ejection of staples from the staple cartridge 40 disposed therein and/or the advancement the knife blade 36 to sever tissue captured between the jaws 32, 34. A person skilled in the art will recognize that various configurations of components for a firing system, mechanical, hydraulic, pneumatic, electromechanical, robotic, or otherwise, can be used to eject staples and/or cut tissue.

As shown in FIG. 2, the end effector 30 of the illustrated implementation has the lower jaw 32 that serves as a cartridge assembly or carrier and the opposed upper jaw 34 that serves as an anvil. The staple cartridge 40, having a plurality of staples therein, is supported in a staple tray 37, which in turn is supported within a cartridge channel of the lower jaw 32. The upper jaw 34 has a plurality of staple forming pockets (not shown), each of which is positioned above a corresponding staple from the plurality of staples contained within the staple cartridge 40. The upper jaw 34 can be connected to the lower jaw 32 in a variety of ways, although in the illustrated implementation the upper jaw 34 has a proximal pivoting end 34*p* that is pivotally received within a proximal end 56*p* of the staple channel 56, just distal to its engagement to the shaft 14. When the upper jaw 34 is pivoted downwardly, the upper jaw 34 moves the anvil surface 33 and the staple forming pockets formed thereon move toward the opposing staple cartridge 40.

Various clamping components can be used to effect opening and closing of the jaws 32, 34 to selectively clamp tissue therebetween. As illustrated, the pivoting end 34*p* of the upper jaw 34 includes a closure feature 34*c* distal to its pivotal attachment with the staple channel 56. Thus, a closure tube 46, whose distal end includes a horseshoe aperture 46*a* that engages the closure feature 34*c*, selectively imparts an opening motion to the upper jaw 34 during proximal longitudinal motion and a closing motion to the upper jaw 34 during distal longitudinal motion of the closure tube 46 in response to the clamping trigger 22. As mentioned above, in various implementations, the opening and closure of the end effector 30 may be effected by relative motion of the lower jaw 32 with respect to the upper jaw 34, relative motion of the upper jaw 34 with respect to the lower jaw 32, or by motion of both jaws 32, 34 with respect to one another.

Figure 3:
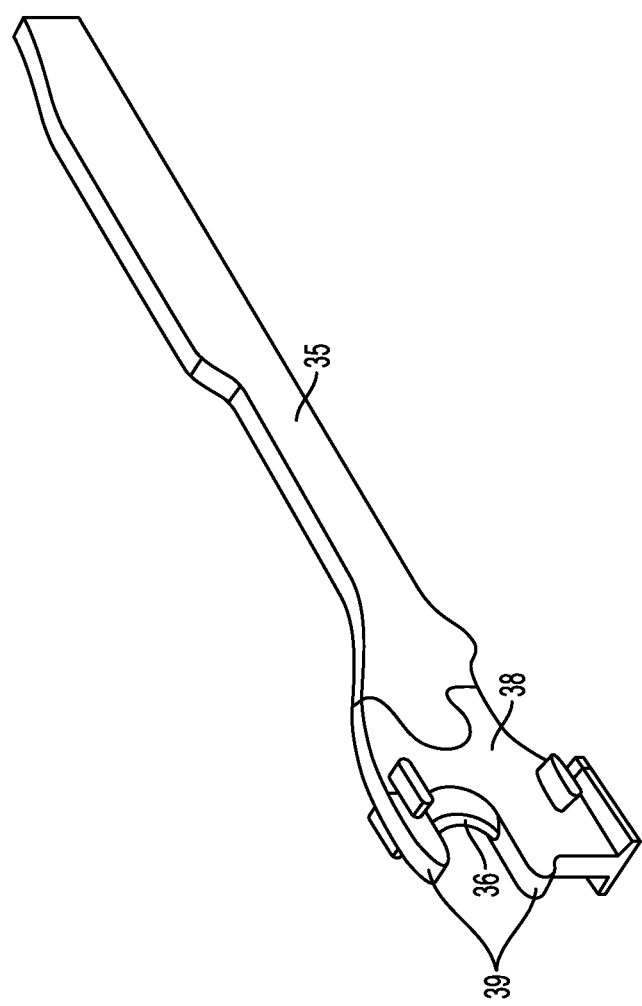
FIG. 3 is a perspective view of a firing bar of the surgical stapler of FIG. 1.

The firing components of the illustrated implementation includes a firing bar 35, as shown in FIG. 3, having an E-beam 38 on a distal end thereof. The firing bar 35 is encompassed within the shaft 14, for example in a longitudinal firing bar slot 14*s* of the shaft 14, and guided by a firing motion from the handle 12. Actuation of the firing trigger 24 can affect distal motion of the E-beam 38 through at least a portion of the end effector 30 to thereby cause the firing of staples contained within the staple cartridge 40. As illustrated, guides 39 projecting from a distal end of the E-Beam 38 can engage a wedge sled 47, shown in FIG. 2, which in turn can push staple drivers 48 upwardly through staple cavities 41 formed in the staple cartridge 40. Upward movement of the staple drivers 48 applies an upward force on each of the plurality of staples within the cartridge 40 to thereby push the staples upwardly against the anvil surface 33 of the upper jaw 34 and create formed staples.

In addition to causing the firing of staples, the E-beam 38 can be configured to facilitate closure of the jaws 32, 34, spacing of the upper jaw 34 from the staple cartridge 40, and/or severing of tissue captured between the jaws 32, 34. In particular, a pair of top pins and a pair of bottom pins can engage one or both of the upper and lower jaws 32, 34 to compress the jaws 32, 34 toward one another as the firing bar 35 advances through the end effector 30. Simultaneously, the knife 36 extending between the top and bottom pins can be configured to sever tissue captured between the jaws 32, 34.

In use, the surgical stapler 10 can be disposed in a cannula or port and disposed at a surgical site. A tissue to be cut and stapled can be placed between the jaws 32, 34 of the surgical stapler 10. Features of the stapler 10 can be maneuvered as desired by the user to achieve a desired location of the jaws 32, 34 at the surgical site and the tissue with respect to the jaws 32, 34. After appropriate positioning has been achieved, the clamping trigger 22 can be pulled toward the stationary handle 20 to actuate the clamping system. The clamping trigger 22 can cause components of the clamping system to operate such that the closure tube 46 advances distally through at least a portion of the shaft 14 to cause at least one of the jaws 32, 34 to collapse towards the other to clamp the tissue disposed therebetween. Thereafter, the firing trigger 24 can be pulled toward the stationary handle 20 to cause components of the firing system to operate such that the firing bar 35 and/or the E-beam 38 are advanced distally through at least a portion of the end effector 30 to effect the firing of staples and optionally to sever the tissue captured between the jaws 32, 34.

Figure 4:
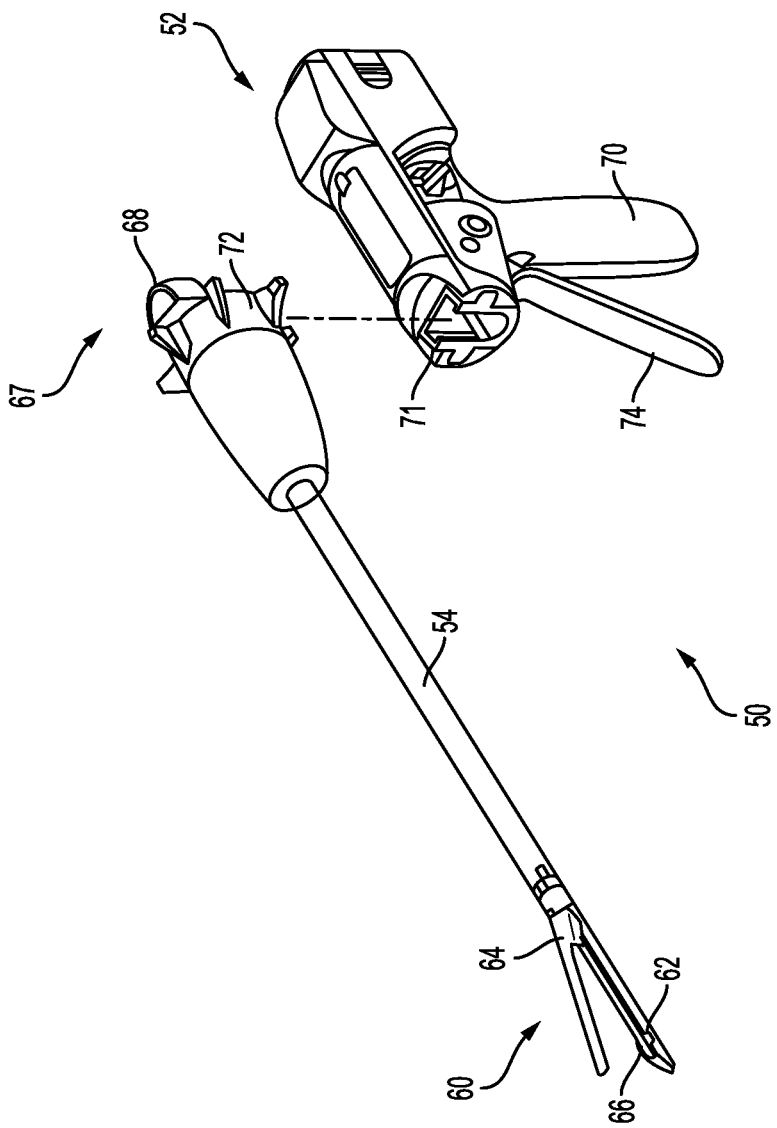
FIG. 4 is a perspective view of another embodiment of a surgical stapler having a modular shaft.

Another example of a surgical instrument in the form of a linear surgical stapler 50 is illustrated in FIG. 4. The stapler 50 can generally be configured and used similar to the stapler 10 of FIG. 1. Similar to the surgical instrument 10 of FIG. 1, the surgical instrument 50 includes a handle assembly 52 with a shaft 54 extending distally therefrom and having an end effector 60 on a distal end thereof for treating tissue. Upper and lower jaws 64, 62 of the end effector 60 can be configured to capture tissue therebetween, staple the tissue by firing of staples from a cartridge 66 disposed in the lower jaw 62, and/or to create an incision in the tissue. In this implementation, an attachment portion 67 on a proximal end of the shaft 54 can be configured to allow for removable attachment of the shaft 54 and the end effector 60 to the handle assembly 52. In particular, mating features 68 of the attachment portion 67 can mate to complementary mating features 71 of the handle assembly 52. The mating features 68, 71 can be configured to couple together via, e.g., a snap fit coupling, a bayonet type coupling, etc., although any number of complementary mating features and any type of coupling can be used to removably couple the shaft 54 to the handle assembly 52. Although the entire shaft 54 of the illustrated implementation is configured to be detachable from the handle assembly 52, in some implementations, the attachment portion 67 can be configured to allow for detachment of only a distal portion of the shaft 54. Detachable coupling of the shaft 54 and/or the end effector 60 can allow for selective attachment of a desired end effector 60 for a particular procedure, and/or for reuse of the handle assembly 52 for multiple different procedures.

The handle assembly 52 can have one or more features thereon to manipulate and operate the end effector 60. By way of non-limiting example, a rotation knob 72 mounted on a distal end of the handle assembly 52 can facilitate rotation of the shaft 54 and/or the end effector 60 with respect to the handle assembly 52. The handle assembly 52 can include clamping components as part of a clamping system actuated by a movable trigger 74 and firing components as part of a firing system that can also be actuated by the trigger 74. Thus, in some implementations, movement of the trigger 74 toward a stationary handle 70 through a first range of motion can actuate clamping components to cause the opposed jaws 62, 64 to approximate toward one another to a closed position. In some implementations, only one of the opposed jaws 62, 24 can move to move the jaws 62, 64 to the closed position. Further movement of the trigger 74 toward the stationary handle 70 through a second range of motion can actuate firing components to cause the ejection of the staples from the staple cartridge 66 and/or the advancement of a knife or other cutting element (not shown) to sever tissue captured between the jaws 62, 64.

Figure 5:
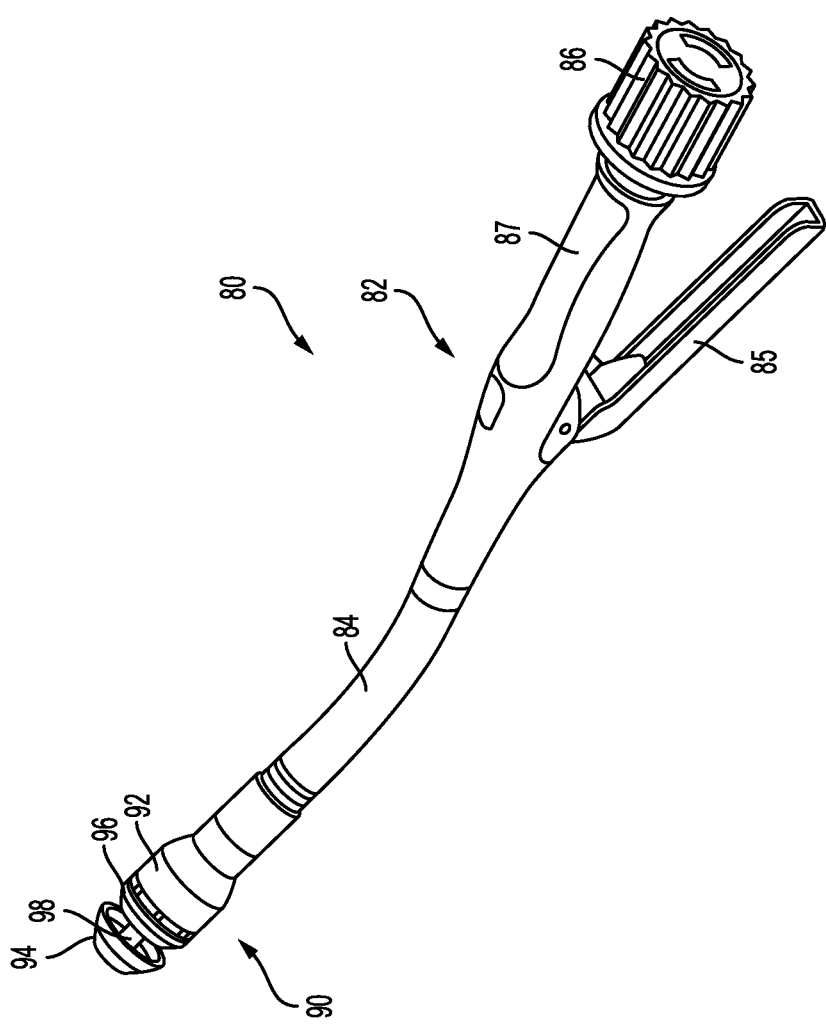
FIG. 5 is a perspective view of one embodiment of a circular surgical stapler.

One example of a surgical instrument in the form of a circular surgical stapler 80 is illustrated in FIG. 5. The stapler 80 can generally be configured and used similar to the linear staplers 10, 50 of FIGS. 1 and 4, but with some features accommodating its functionality as a circular stapler. Similar to the surgical instruments 10, 50, the surgical instrument 80 includes a handle assembly 82 with a shaft 84 extending distally therefrom and having an end effector 90 on a distal end thereof for treating tissue. The end effector 90 can include a cartridge assembly 92 and an anvil 94, each having a tissue-contacting surface that is substantially circular in shape. The cartridge assembly 92 and the anvil 94 can be coupled together via a shaft 98 extending from the anvil 94 to the handle assembly 82 of the stapler 80, and manipulating an actuator 85 on the handle assembly 82 can retract and advance the shaft 98 to move the anvil 94 relative to the cartridge assembly 92. The anvil 94 and cartridge assembly 92 can perform various functions and can be configured to capture tissue therebetween, staple the tissue by firing of staples from a cartridge 96 of the cartridge assembly 92 and/or can create an incision in the tissue. In general, the cartridge assembly 92 can house a cartridge containing the staples and can deploy staples against the anvil 94 to form a circular pattern of staples, e.g., staple around a circumference of a tubular body organ.

In one implementation, the shaft 98 can be formed of first and second portions (not shown) configured to releasably couple together to allow the anvil 94 to be detached from the cartridge assembly 92, which may allow greater flexibility in positioning the anvil 94 and the cartridge assembly 92 in a body of a patient. For example, the first portion of the shaft 98 can be disposed within the cartridge assembly 92 and extend distally outside of the cartridge assembly 92, terminating in a distal mating feature. The second portion of the shaft 98 can be disposed within the anvil 94 and extend proximally outside of the cartridge assembly 92, terminating in a proximal mating feature. In use, the proximal and distal mating features can be coupled together to allow the anvil 94 and cartridge assembly 92 to move relative to one another.

The handle assembly 82 of the stapler 80 can have various actuators disposed thereon that can control movement of the stapler. For example, the handle assembly 82 can have a rotation knob 86 disposed thereon to facilitate positioning of the end effector 90 via rotation, and/or the trigger 85 for actuation of the end effector 90. Movement of the trigger 85 toward a stationary handle 87 through a first range of motion can actuate components of a clamping system to approximate the jaws, i.e. move the anvil 94 toward the cartridge assembly 92. Movement of the trigger 85 toward the stationary handle 87 through a second range of motion can actuate components of a firing system to cause the staples to deploy from the staple cartridge assembly 92 and/or cause advancement of a knife to sever tissue captured between the cartridge assembly 92 and the anvil 94.

The illustrated examples of surgical stapling instruments 10, 50, 80 provide only a few examples of many different configurations, and associated methods of use, that can be used in conjunction with the disclosures provided herein. Although the illustrated examples are all configured for use in minimally invasive procedures, it will be appreciated that instruments configured for use in open surgical procedures, e.g., open linear staplers as described in U.S. Pat. No. 8,317,070 entitled "Surgical Stapling Devices That Produce Formed Staples Having Different Lengths" and filed Feb. 28, 2007, can be used in conjunction with the disclosures provided herein. Greater detail on the illustrated examples, as well as additional examples of surgical staplers, components thereof, and their related methods of use, are provided in U.S. Pat. Pub. No. 2015/0277471 entitled "Systems And Methods For Controlling A Segmented Circuit" and filed Mar. 26, 2014, U.S. Pat. Pub. No. 2013/0256377 entitled "Layer Comprising Deployable Attachment Members" and filed Feb. 8, 2013, U.S. Pat. No. 8,393,514 entitled "Selectively Orientable Implantable Fastener Cartridge" and filed Sep. 30, 2010, U.S. Pat. No. 8,317,070 entitled "Surgical Stapling Devices That Produce Formed Staples Having Different Lengths" and filed Feb. 28, 2007, U.S. Pat. No. 7,143,925 entitled "Surgical Instrument Incorporating EAP Blocking Lockout Mechanism" and filed Jun. 21, 2005, U.S. Pat. Pub. No. 2015/0134077 entitled "Sealing Materials For Use In Surgical Stapling" and filed Nov. 8, 2013, entitled "Sealing Materials for Use in Surgical Procedures," and filed on Nov. 8, 2013, U.S. Pat. Pub. No. 2015/0134076, entitled "Hybrid Adjunct Materials for Use in Surgical Stapling," and filed on Nov. 8, 2013, U.S. Pat. Pub. No. 2015/0133996, entitled "Positively Charged Implantable Materials and Method of Forming the Same," and filed on Nov. 8, 2013, U.S. Pat. Pub. No. 2015/0129634, entitled "Tissue Ingrowth Materials and Method of Using the Same," and filed on Nov. 8, 2013, U.S. Pat. Pub. No. 2015/0133995, entitled "Hybrid Adjunct Materials for Use in Surgical Stapling," and filed on Nov. 8, 2013, U.S. Pat. Pub. No. 2015/0272575, entitled "Surgical Instrument Comprising a Sensor System," and filed on Mar. 26, 2014, and U.S. Pat. Pub. No. 2015/0351758, entitled "Adjunct Materials and Methods of Using Same in Surgical Methods for Tissue Sealing," and filed on Jun. 10, 2014, which are hereby incorporated by reference herein in their entireties.

Implantable Adjuncts

As indicated above, various implantable adjuncts are provided for use in conjunction with surgical stapling instruments. The adjuncts can have a variety of configurations, and can be formed from various materials. In general, an adjunct can be formed from one or more of a film, a foam, an injection molded thermoplastic, a vacuum thermoformed material, a fibrous structure, and hybrids thereof. The adjunct can also include one or more biologically-derived materials and one or more drugs. Each of these materials is discussed in more detail below.

An adjunct can be formed from a foam, such as a closed-cell foam, an open-cell foam, or a sponge. An example of how such an adjunct can be fabricated is from animal derived collagen, such as porcine tendon, that can then be processed and lyophilized into a foam structure. Gelatin can also be used and processed into a foam. Examples of various foam adjuncts are further described in previously mentioned U.S. Pat. No. 8,393,514 entitled "Selectively Orientable Implantable Fastener Cartridge" and filed Sep. 30, 2010.

An adjunct can also be formed from a film formed from any suitable material or combination thereof discussed below. The film can include one or more layers, each of which can have different degradation rates. Furthermore, the film can have various regions formed therein, for example, reservoirs that can releasably retain therein one or more medicants in a number of different forms. The reservoirs having at least one medicant disposed therein can be sealed using one or more different coating layers which can include absorbable or non-absorbable polymers. The film can be formed in various ways. For example, it can be an extruded or a compression molded film. The medicants can also be absorbed onto the film or bound to the film via non-covalent interactions such as hydrogen bonding.

An adjunct can also be formed from injection molded thermoplastic or a vacuum thermoformed material. Examples of various molded adjuncts are further described in U.S. Pat. Pub. No. 2013/0221065 entitled "Fastener Cartridge Comprising A Releasably Attached Tissue Thickness Compensator" and filed Feb. 8, 2013, which is hereby incorporated by reference in its entirety. The adjunct can also be a fiber-based lattice which can be a woven fabric, knitted fabric or non-woven fabric such as a melt-blown, needle-punched or thermal-constructed loose woven fabric. An adjunct can have multiple regions that can be formed from the same type of lattice or from different types of lattices that can together form the adjunct in a number of different ways. For example, the fibers can be woven, braided, knitted, or otherwise interconnected so as to form a regular or irregular structure. The fibers can be interconnected such that the resulting adjunct is relatively loose. Alternatively, the adjunct can include tightly interconnected fibers. The adjunct can be in a form of a sheet, tube, spiral, or any other structure that can include compliant portions and/or more rigid, reinforcement portions. The adjunct can be configured such that certain regions thereof can have more dense fibers while others have less dense fibers. The fiber density can vary in different directions along one or more dimensions of the adjunct, based on an intended application of the adjunct. The adjunct can be formed from woven, knitted, or otherwise interconnected fibers, which allows the adjunct to be stretched. For example, the adjunct can be configured to stretch in a direction along its longitudinal axis and/or in a lateral direction that is perpendicular to the longitudinal axis. While being stretchable in at least two dimensions (e.g., X and Y directions), the adjunct can provide reinforcement along its thickness (e.g., in a Z direction) such that it stretches but resists tearing and pull-through by the staples. Non-limiting examples of adjuncts that are configured to be implanted such that they can stretch with the tissue are described in the above-mentioned U.S. Pat. Pub. No. 2016/0089142 entitled "Method for Creating a Flexible Staple Line," filed on Sep. 26, 2014, which is hereby incorporated by reference herein in its entirety.

The adjunct can also be a hybrid construct, such as a laminate composite or melt-locked interconnected fiber. Examples of various hybrid construct adjuncts are further described in U.S. Pat. No. 9,282,962 entitled "Adhesive Film Laminate" and filed Feb. 8, 2013, and in U.S. Pat. No. 7,601,118 entitled "Minimally Invasive Medical Implant And Insertion Device And Method For Using The Same" and filed Sep. 12, 2007, which are hereby incorporated by reference in their entireties.

The adjuncts in accordance with the described techniques can be formed from various materials. The materials can be used in various embodiments for different purposes. The materials can be selected in accordance with a desired therapy to be delivered to tissue so as to facilitate tissue in-growth. The materials can include bioabsorbable and biocompatible polymers, including homopolymers and copolymers. Bioabsorbable polymers can be absorbable, resorbable, bioresorbable, or biodegradable polymers. An adjunct can also include active agents, such as active cell culture (e.g., diced autologous tissue, agents used for stem cell therapy (e.g., Biosutures and Cellerix S.L.), hemostatic agents, and tissue healing agents.

The adjuncts can releasably retain therein at least one medicant that can be selected from a large number of different medicants. Medicants include, but are not limited to, drugs or other agents included within, or associated with, the adjuncts that have a desired functionality. The medicants include, but are not limited to, for example, antimicrobial agents such as antibacterial and antibiotic agents, antifungal agents, antiviral agents, anti-inflammatory agents, growth factors, analgesics, anesthetics, tissue matrix degeneration inhibitors, anti-cancer agents, hemostatic agents, and other agents that elicit a biological response. The adjuncts can also be made from or include agents that enhance visibility during imaging, such as, for example, echogenic materials or radio-opaque materials.

Examples of various adjuncts and various techniques for releasing medicants from adjuncts are further described in U.S. patent application Ser. No. 14/840,613 entitled "Medicant Eluting Adjuncts and Methods of Using Medicant Eluting Adjuncts" and filed Aug. 31, 2015, which is hereby incorporated by reference in its entirety.

Adjunct Attachment

Various exemplary devices, systems and methods are provided for releasably retaining a frame with an adjunct to a jaw of an end effector of a surgical instrument. In certain exemplary embodiments, the frame can include retaining features for coupling an adjunct to a tissue-facing surface of the frame, thereby releasably coupling the adjunct material to the jaw of the end effector. In some implementations, the frame can include a plurality of retaining features that are configured to engage the adjunct material thereby creating a tension in the adjunct material, which can further assist with securing the frame to the jaw. The frame can also include various attachment features (e.g., attachment arms) that are configured to assist with releasably coupling the frame to the jaw.

In other embodiments, a removable applicator can be member provided for retaining at least one adjunct material and for aligning and coupling the adjunct material to a frame that is already secured to the jaw. Thus, in some implementations the jaws can be manipulated to engage the adjunct material retained by the applicator member, thereby mounting the adjunct onto the end effector. In particular, a force applied to the applicator member can cause the applicator member to release the at least one adjunct material and to transfer the at least one adjunct material to at least one respective frame secured to a jaw of the end effector.

FIGS. 6A and 6B illustrate one exemplary embodiment of a frame 100 that configured to releasably couple to an upper jaw 102 of an end effector and to releasably retain an adjunct material (not shown) on a tissue-facing surface 105 of the frame 100. As shown, the frame 100 can be in the form of an elongated body 106 having an outward facing surface 108 that can mate to and extend along an anvil surface 103 of an anvil of the upper jaw 102. One or more pairs of attachment arms 110 can extend from the elongated body 106, with each pair of attachment arms 110 extending from opposing sides of the elongated body 106 and arching towards a longitudinal axis of the elongated body 106. The attachment arms 110 can have a shape that is similar to an outer profile of the outward facing surface of the upper jaw 102, thereby allowing the attachment arms to extend around a part of the outward facing surface of the upper jaw 102 for securing the frame 110 to the upper jaw 102. Although the frame 110 is shown and described as being configured for releasably securing to the upper jaw 102, the frame 100 can be configured for releasably securing to the upper jaw and/or lower jaw without departing from the scope of this disclosure.

Some embodiments of the attachment arms 110 can be made out of a compliant and or elastic material that allows the attachment arms 110 to deform or spread apart. The compliant and/or elastic attachment arms 110 can assist with coupling the frame 100 to the upper jaw 102, as well as provide a compressive force against the outward facing surface of the upper jaw 102 thereby securing the attachment and position of the frame 100 to the upper jaw 102. For example, the frame 100 can be coupled to the upper jaw 102 by guiding a distal end of the upper jaw 102 through a space created by the attachment arms 110 and/or spreading the attachment arms 110 to allow the upper jaw 102 to be positioned within the arcs of the attachment arms 110.

The frame 100 can be made out of one or more of a variety of materials, including compliant and/or elastic materials. For example, the frame can be made out of any number of materials (e.g., surgical grade), such as metals and polymers, without departing the scope of this disclosure.

In some embodiments, the upper jaw 102 and/or frame 100 can include a locking mechanism that assists with releasably securing the frame 100 to the upper jaw 102. For example, the upper jaw 102 can include a locking feature at a proximal end that interacts and locks the frame 100 to the upper jaw 102 when the frame 100 is loaded onto the upper jaw 102. Furthermore, the upper jaw 102 and/or frame 100 can include a release feature (e.g., shown as a tab 107 in FIG. 6B) that is configured to force or allow the release of the frame 100 from the upper jaw 102 when acted upon (e.g., pushed or pivoted).

As discussed above, the tissue facing surface 105 of the frame 100 can be configured to releasably secure an adjunct material thereto for allowing the adjunct material to be stapled to tissue and to remain at a surgical site. The frame 100 can be configured such that the adjunct material can be secured to the frame 100, however, the adjunct material can also be uncoupled from the frame 100 thereby allowing the adjunct material, and not the frame 100, to remain at the surgical site. Various attachment techniques can be utilized to mate an adjunct to the frame, such as an adhesive, fasteners, or any other chemical or mechanical attachment techniques.

FIGS. 7A-7E illustrate another embodiment of a frame 200 that can be releasably coupled to a jaw of an end effector, such as an upper jaw 202. The frame 200 can be configured to releasably retain an adjunct material 220 to thereby releasably secure the adjunct material 220 to the upper jaw 202. Similar to the embodiment above, the frame 200 can be coupled to either the upper and/or lower jaw without departing from the scope of this disclosure. As shown in FIGS. 7B-7E, the frame 200 can include attachment arms 210 that extend from an elongated body 206 of the frame 200 and that can be shaped to conform to an outward facing surface of the upper jaw 202. As such, the attachment arms 210 can assist with securing the position of the frame 200 and adjunct 220 relative to the upper jaw 202, such as before and during firing of staples.

As shown, the tissue facing surface 205 of the frame 200 can include a plurality of retaining features 222 positioned along the length of the elongated body 206. The plurality of retaining features 222 can be configured to releasably secure the adjunct material 220 to the frame 200 such that the adjunct material 220 can remain securely coupled to the frame 200 at least until firing of a knife along the end effector thereby cutting the adjunct material 220. The retaining features 222 can be shaped and engaged with the adjunct material 220 such that they allow the adjunct material 220 to release attachment from the frame 200 after the adjunct material 220 has been cut and as the end effector moves away from the surgical site after firing of the staples. The frame 200 can remain coupled to the end effector, such as the upper jaw, as the adjunct is released. A user can subsequently decouple the frame 200 from the jaw or load another adjunct material 220 onto the frame 200. As such, the frame 200 is configured such that the adjunct material 220 is allowed to remain at the surgical site and the frame 200 remains attached to the end effector so that the frame 200 is not left at the surgical site and can either be reused or disposed of.

As shown in FIG. 7A, the frame 200 can include at least one slot or opening 226 that extends along a length of the elongate body 206. Each opening 226 can be configured to allow staples to pass therethrough and into the adjunct and tissue engaged between the jaws, thereby stapling the adjunct material 220 to adjacent tissue. The openings 226 can be shaped such that they surround the staple cavities of the cartridge and/or staple forming cavities of the anvil surface thereby allowing the firing of the staples without the frame 200 interfering or getting stapled to tissue.

Figure 7C:
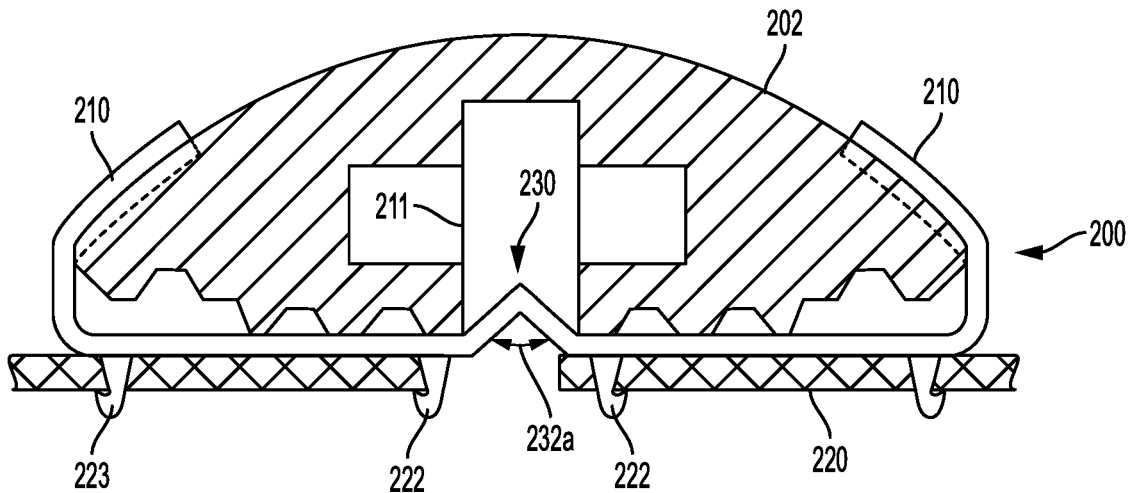
FIG. 7C is a cross section view of the frame coupled to the jaw of FIG. 7B, with the frame having a plurality of retaining features that secure the adjunct material to the tissue-facing surface of the frame.
Figure 7D:
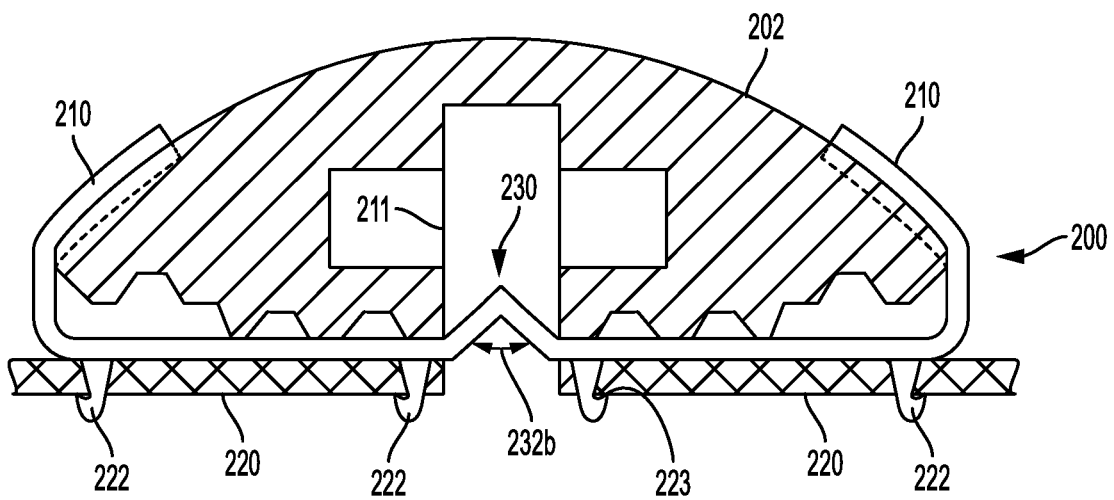
FIG. 7D is a cross section view of the frame coupled to the jaw of FIG. 7B.

The frame 200 can also include a hinge 230 along a length of the elongate body 206 that allows the elongate body 206 to apply tension to the adjunct. As shown in FIG. 7A, the hinge 230 can extend along a longitudinal axis of the elongated body 206 and can include a V-shaped profile. The V-shaped hinge 230 can be configured to extend a distance within a knife slot 211 of the upper jaw 202 when the frame is coupled to the upper jaw, as shown in FIGS. 7C-7D. This can allow a knife to advance along the knife slot 211 and cut the adjunct material 220 without interference from the frame 200. In an exemplary embodiment, however, the hinge 230 can be formed from a material that can be cut by the knife as it is advanced through the knife slot 211. Cutting of the hinge 230 can assist with releasing the buttress from the frame 200, as will be discussed in more detail below.

FIGS. 7C-7D illustrate the frame 200 coupled to the upper jaw, with the hinge 230 extending into the knife slot 211. The adjunct material 220 is also shown coupled to a plurality of retaining features 222. The retaining features 222 can be made out of a rigid, semi-rigid, or flexible material and can include a hook or securing feature 223 that extends outward away from the longitudinal axis of the elongate body 206. This configuration of the retaining features 222 can allow a first side of the adjunct material 220 to be secured to a plurality of retaining features 222 positioned on a first side of the hinge 230. The adjunct material 220 can then be pulled so that it is under tension before securing a second side of the adjunct material 220 to the retaining features 222 positioned on a second side of the hinge 230, as shown in FIG. 7C. The retaining features 222 on the first side of the hinge 230 can thus pull in an opposite direction from the retaining features 222 on the second side of the hinge 230 thereby placing the adjunct material under tension. The retaining features 222 can also deform or bend when the adjunct material 220 is under tension thereby further securing the adjunct material 220 to the frame 200. Furthermore, having the retaining features engage the adjunct material 220 under tension can pull opposing sides of the elongate body 206 closer together thereby allowing the hinge 230 to form a first angle 232a and further securing the frame 200 to the upper jaw 202.

As mentioned above, a knife can be advanced along the knife slot 211 thereby cutting the adjunct material 220 as well as cutting at least part of the hinge 230. By cutting the adjunct material 220 positioned adjacent the knife slot 211, the tension in the adjunct material 220 caused by the retaining features 222 pulling on the adjunct material from opposing sides of the knife slot 211 can be released. When this tension along the adjunct material 220 is released, the retaining features 222 can reform (e.g., straighten) thereby allowing the adjunct material 220 to be pulled off of the frame, such as after being stapled. The opposing sides of the elongate body to 205 can also move further apart when the tension along the adjunct material 220 is released, which can allow the hinge 230 to form a second angle 232b (see FIG. 7D). The second angle 232b can be larger than the first angle 232a thereby allowing the opposing sides of the elongate body 206 to move further apart from each other, such as for allowing a user to decouple the frame 200 from the upper jaw 202. Similarly, if a part of the hinge 230 is cut, the opposing sides of the elongate body 206 can move further apart to allow a user to decouple the frame from the upper jaw 202. In some embodiments, the frame can include an adhesive and/or one or more features that can couple to a part of the knife slot to further assist in securing the frame to the upper jaw 202.

Figure 7E:
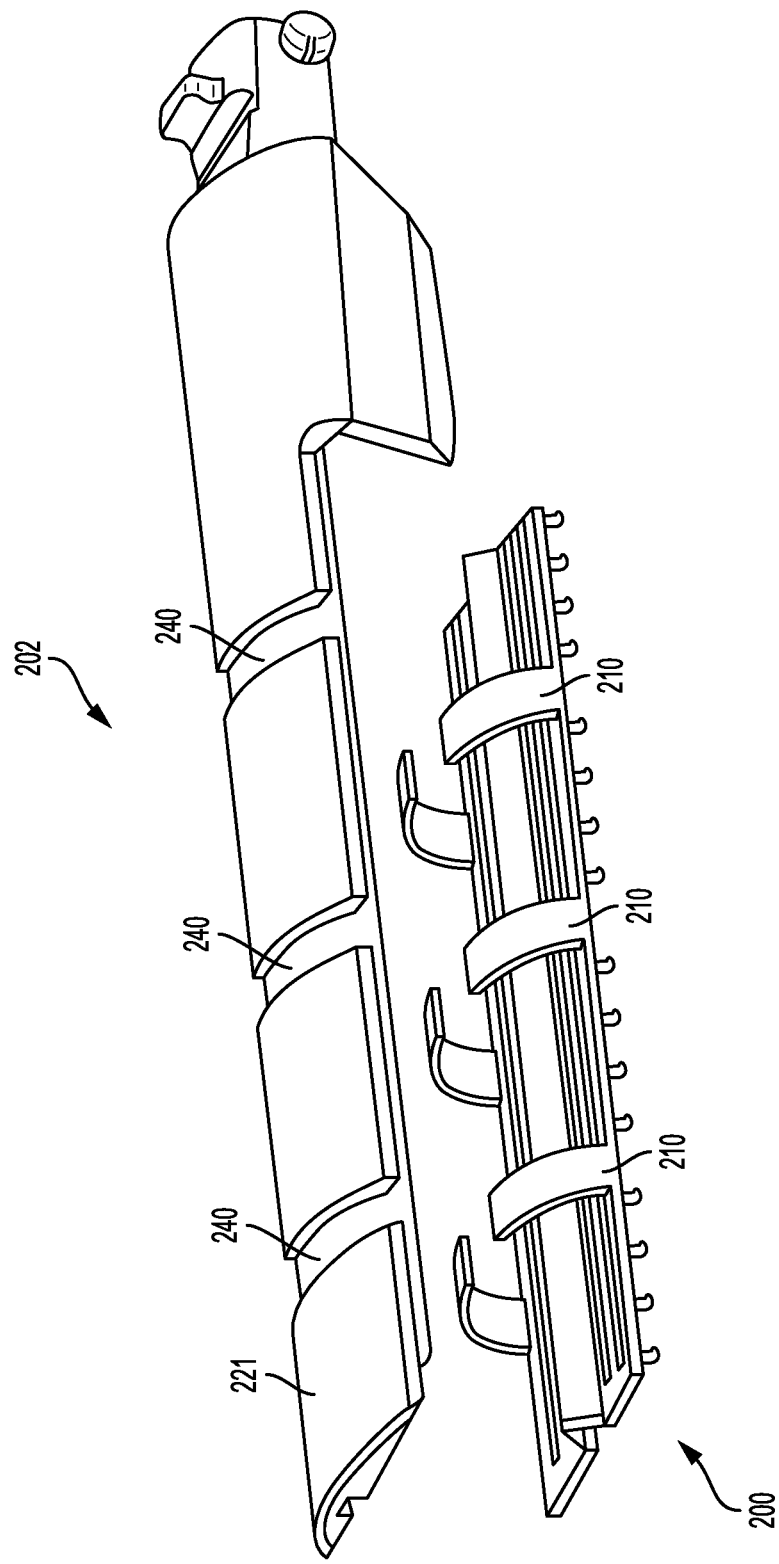
FIG. 7E is an exploded view of the frame of FIG. 7A and the jaw showing an outward facing surface of the jaw having attachment arm features.

FIG. 7E illustrates the outward facing surface 221 of the upper jaw 202 having attachment arm coupling features 240 therealong that are configured to prevent attachment arms 210 of the frame 200 from moving relative to a length of the upper jaw 202, such as when the frame 200 is coupled to the upper jaw 202. As shown, each attachment arm coupling feature 240 can include a recess that has a shape and depth that allows an attachment arm 210 to be seated therein to prevent the attachment arm 210 from sliding out of the attachment arm coupling features 240 and/or along the length of the upper jaw 202. For example, the attachment arm coupling feature 240 can be in the form of a recessed band that extends at an arc perpendicular to the longitudinal axis of the upper jaw.

Because the attachment arm coupling features 240 can prevent the frame 200 from sliding along the upper jaw 202 even during loading of the frame 200 onto the upper jaw 202, the frame 200 can be snapped on by deforming (e.g., elastically) the attachment arms 210 to allow the upper jaw 202 to fit within the confines of the attachment arms 210. The attachment arms can be aligned with the attachment arm coupling features 240 such that each of the attachment arms 210 can spring towards the outward facing surface and into a corresponding attachment arm coupling feature 240. Once coupled, the attachment arms 210 and attachment arm coupling features 240 can prevent the frame 200 from sliding along the upper jaw 202 thereby ensuring a desired positioning of the adjunct material 220 relative to the upper jaw 202.

As mentioned above, the frames 100, 200 can be configured to mate to either the upper and/or lower jaws. In addition, a frame can be coupled or mounted to a jaw of an end effector prior to having an adjunct coupled to the frame. As such, a user may need to align and mount an adjunct material to the frame when the frame is coupled to the jaw. Some frames can be reusable such that more than one adjunct can be used with a single frame. FIGS. 8A-8B illustrate a reusable frame that can be coupled to either the upper or lower jaw of the end effector and, as shown in FIG. 8C, an applicator member can be used to position and assist with mounting at least one adjunct material onto a respective frame coupled to either the upper or lower jaw.

FIG. 8A illustrates an embodiment of a frame 300 including an overlay 350 that is configured to extend along a part of an upper jaw 302. In some embodiments, the overlay 350 can include a flexible elongated tubular member that can slide over the upper jaw 302 thereby covering an anvil surface 303 of the upper jaw 302. In some embodiments, the overlay 350 can include an elongated surface that can cover the anvil surface 303 and can further include edges that wrap around one or more sides of the upper jaw to thereby secure the overlay to the upper jaw. The overlay 350 can further include an adhesive material that can assist with securing the position of the overlay 350 relative to the upper jaw 302. A tissue facing surface 305 of the overlay 350 can include at least one row of retaining features 322 that are configured to assist with coupling an adjunct material 320 thereto. For example, the tissue facing surface 305 of the overlay 350 can include two rows of retaining features 322 with each row positioned along opposing sides of the anvil surface 303 when the overlay 350 is coupled to the upper jaw 302.

FIG. 8B illustrates the upper and lower jaws 302, 304 each having an overlay 350a, 350b covering an outer surface thereof. As shown in FIG. 8B, an adjunct material 320 can be releasably mated to both of the upper and lower jaws 302, 304. The adjunct material 320 can include at least one row of complimentary retaining features 325 that are configured to engage and releasably secure to at least one row of retaining features 322 along the overlay 350. For example, the adjunct material 320 can include two rows of complimentary retaining features 325, with each row positioned along opposing sides of the adjunct material 320 such that they align with the two rows of retaining features 322 along the overlay 350, as shown in FIG. 8B. As such, the adjunct material 320 can be coupled to an overlay 350 by aligning the rows of retaining features 322 along the overlay 350 with the rows of complimentary retaining features 325 along the adjunct material 320. Once aligned, the retaining features 322 and complimentary retaining features 325 can be engaged thereby releasably securing the adjunct material 320 to the overlay 350. The engagement between the retaining features 322 and complimentary retaining features 325 can be strong enough to maintain the position of the adjunct material 320 relative to the overlay 350 prior to firing of staples, while allowing the adjunct material 320 to uncouple and remain stapled at the surgical site after firing of the staples. The retaining features 322 and/or complimentary retaining features 325 can have various configurations, such as hook and loop members, various self-adhering materials, snap-fit features, etc. Furthermore, although the retaining features 322 and complimentary retaining features 325 are shown and described as being formed into rows along the overlay and adjunct material 320, respectively, the retaining features 322 and complimentary retaining features 325 can have any number of shapes and configurations. For example, positioning retaining features 322 and complimentary retaining features 325 along opposing sides of the anvil surface 203 (when the overlay 350 is coupled to the upper jaw) allows the retaining features 322 and complimentary retaining features 325 to not interfere with either the advancing of the knife and/or firing of staples, however, other configurations can also achieve this.

Applicator

One or both of the adjunct materials 320 can be releasably retained on the overlays 350a, 350b coupled to the upper and lower jaws 302, 304, respectively, using an applicator member 360 shown in FIG. 8C. The applicator member 360 can be in the form of a frame-like holder configured to releasably retain one or both of the adjunct materials 320a, 320b. In the illustrated example, the applicator member 360 is in the form of first (e.g., bottom) and second (e.g., top) generally rectangular housings 324, 326 coupled to one another as shown in FIG. 8C. As also shown in FIG. 8C, the first and second housing 324, 326 can engage edges of the long sides of the adjunct materials 320a, 320b therebetween. In other words, the applicator member 360 can be in the shape of a generally U-shaped frame that surrounds an outer perimeter of at least two sides (e.g., long sides) of one or two adjunct materials. In particular, as shown in FIG. 8C, the applicator member 360 can expose the complimentary retaining features 325 thereby allowing the complimentary retaining features 325 to align with and couple to the retaining features 322 along the overlay 350. It should be appreciated that the adjunct materials 320a, 320b and the first and second housings 324, 326 of the applicator member 360 encompassing them can be symmetrical. Thus, either of the adjunct materials 320a, 320b can be applied to either overlay 350a, 350b coupled to the upper or lower jaw 302, 304, respectively.

The applicator member 360 can be formed from any suitable material (e.g., plastic), and its walls can be relatively thin and it can be disposable. In use, to transfer the adjunct materials 320a, 320b to the overlays 350a, 350b, respectively, the upper or lower jaws 302, 304 can be clamped together into the opening in the applicator member 360, with the complimenting retaining features 325 of the adjunct materials 320a, 320b aligned with the retaining features 322 along the overlays 350a, 350b. In this way, force applied by the jaws 302, 304 can cause the adjunct materials 320a, 320b to separate from the applicator member 360 and to be engaged with the overlays 350a, 350b. In particular, in this example, as force is applied to the applicator member 360 by the jaws 302, 304 of the end effector, the complimentary retaining features 325 of the adjunct materials 320a, 320b are securely coupled to the retaining features 322 along the overlays 350a, 350b.

After the adjunct materials 320a, 320b are transferred to the overlays positioned over the upper and lower jaws 302, 304, the jaws can be opened and the applicator member 360 can be separated from the end effector. The overlays 350a, 350b attached to the upper and lower jaws 302, 304 can thus be mated with their respective adjunct materials 320a, 320b, as shown in FIG. 8B, and can then be used as desired in a surgical procedure.

It should be appreciated that the applicator member 360 is shown to releasably retain two adjunct materials 320a, 320b by way of example only, and the applicator member 360 or a similar component configured to releasably hold at least one adjunct material 320 can be used to transfer an adjunct material 320 only to a single frame or overlay coupled to the end effector. Moreover, the applicator member can be used to attach one or more adjuncts to any of the frames and/or jaws disclosed herein.

A person skilled in the art will appreciate that the present invention has application in conventional minimally-invasive and open surgical instrumentation as well application in robotic-assisted surgery. Furthermore, the devices disclosed herein can be designed to be disposed of after a single use, or they can be designed to be used multiple times. In either case, however, the device can be reconditioned for reuse after at least one use. Reconditioning can include any combination of the steps of disassembly of the device, followed by cleaning or replacement of particular pieces and subsequent reassembly. In particular, the device can be disassembled, and any number of the particular pieces or parts of the device can be selectively replaced or removed in any combination. Upon cleaning and/or replacement of particular parts, the device can be reassembled for subsequent use either at a reconditioning facility, or by a surgical team immediately prior to a surgical procedure. Those skilled in the art will appreciate that reconditioning of a device can utilize a variety of techniques for disassembly, cleaning/replacement, and reassembly. Use of such techniques, and the resulting reconditioned device, are all within the scope of the present application.

One skilled in the art will appreciate further features and advantages of the invention based on the above-described embodiments. Accordingly, the invention is not to be limited by what has been particularly shown and described, except as indicated by the appended claims. All publications and references cited herein are expressly incorporated herein by reference in their entirety.

What is claimed is:

1. An end effector for a surgical instrument, comprising:
   first and second jaws movably coupled to one another and configured to engage tissue therebetween and to fire a plurality of surgical staples into the tissue;
   a frame configured to releasably engage the first jaw; and
   an adjunct material releasably secured to a tissue-facing surface of the frame;
   wherein at least a portion of the tissue-facing surface of the frame is vertically aligned with the adjunct material and the first jaw when the frame is releasably engaged to the first jaw; and
   wherein the frame remains releasably engaged to the first jaw after release of the adjunct therefrom.

2. The end effector of claim 1, wherein the frame comprises an overlay configured to extend along a part of the first jaw.

3. The end effector of claim 2, wherein the overlay includes an adhesive for securing a position of the overlay relative to the first jaw.

4. The end effector of claim 2, wherein the overlay is flexible.

5. The end effector of claim 2, wherein the overlay includes at least one row of retaining features arranged to correspond with at least one row of complimentary retaining features positioned along the adjunct material for coupling the adjunct material to the overlay.

6. The end effector of claim 5, wherein the at least one row of complimentary retaining features extends along opposing sides of the adjunct material between distal and proximal ends of the adjunct material.

7. A method for stapling tissue, comprising:
   releasably coupling a frame to a first jaw of an end effector, the frame having an adjunct material releasably secured thereto;
   engaging tissue between the first jaw and a second jaw of the end effector; and
   activating the end effector to fire a plurality of staples through the adjunct and into the tissue,
   wherein the firing causes the adjunct material to release from the frame such that the adjunct material remains stapled to the tissue; and
   wherein, with the frame releasably coupled to the first jaw, at least a portion of a tissue-facing surface of the frame is vertically aligned with the adjunct and the first jaw.

8. The method of claim 7, wherein the frame comprises an overlay that is releasably adhered to the first jaw.

9. The method of claim 7, wherein the frame remains releasably coupled to the first jaw after the firing.

10. The method of claim 7, wherein activating the end effector does not fire the plurality of staples through the frame.

* * * * *